(12) United States Patent
Bordeau et al.

(10) Patent No.: US 9,078,859 B2
(45) Date of Patent: Jul. 14, 2015

(54) USE OF A SYNERGISTIC COMBINATION OF HYPOTHIOCYANITE AND/OR HYPOHALITE IONS AND LACTOFERRIN FOR PREPARING A TREATMENT FOR CYSTIC FIBROSIS

(75) Inventors: Philippe Bordeau, Meyzieu (FR); Jean-Paul Perraudin, Brussels (BE)

(73) Assignee: ALAXIA, Lyons (FR)

( * ) Notice: Subject to any disclaimer, the term of this patent is extended or adjusted under 35 U.S.C. 154(b) by 364 days.

(21) Appl. No.: 13/146,779

(22) PCT Filed: Jan. 28, 2010

(86) PCT No.: PCT/FR2010/000070
§ 371 (c)(1),
(2), (4) Date: Oct. 4, 2011

(87) PCT Pub. No.: WO2010/086530
PCT Pub. Date: Aug. 5, 2010

(65) Prior Publication Data
US 2012/0021071 A1    Jan. 26, 2012

(30) Foreign Application Priority Data

Jan. 28, 2009 (FR) ..................................... 09 50536

(51) Int. Cl.
| | | |
|---|---|---|
| *A61K 38/40* | (2006.01) | |
| *A61K 33/04* | (2006.01) | |
| *A61P 11/00* | (2006.01) | |
| *A61P 31/04* | (2006.01) | |
| *A61K 33/18* | (2006.01) | |

(52) U.S. Cl.
CPC ................. *A61K 33/18* (2013.01); *A61K 38/40* (2013.01)

(58) Field of Classification Search
None
See application file for complete search history.

(56) References Cited

U.S. PATENT DOCUMENTS

| | | | |
|---|---|---|---|
| 4,791,193 A * | 12/1988 | Okonogi et al. | ............... 530/416 |
| 8,263,138 B2 * | 9/2012 | Perraudin | ..................... 424/661 |
| 2002/0172645 A1 | 11/2002 | Conner | |
| 2009/0029921 A1 * | 1/2009 | Ward et al. | ...................... 514/12 |

FOREIGN PATENT DOCUMENTS

| | | |
|---|---|---|
| WO | WO 2005/113026 A2 | 12/2005 |
| WO | WO 2007/134180 A2 | 11/2007 |
| WO | WO 2008/003688 A1 | 1/2008 |
| WO | WO 2008003688 A1 * | 1/2008 |

OTHER PUBLICATIONS

Press Release by Alaxia, "Meveol by Alaxia is granted orphan drug status for the treatment of cystic fibrosis in EU", Sep. 2, 2009, http://www.prlog.org/10329509-meveol-by-alaxia-is-granted-orphan-drug-status-for-the-treatment-of-cystic-fibrosis-in-eu.html.*
Rogan et al., "Loss of Microbicidal Activity and Increased Formation of Biofilm Due to Decreased Lactoferrin Activity in Patients with Cystic Fibrosis," The Jounral of Infectious Diseases, 2004; 190:1245-1253.*
Singh et al., "A component of innate immunity prevents bacterial biofilm development," letters to nature, Nature, vol. 417, May 30, 2002, p. 552-555.*
Gerson et al., "The Lactoperoxidase System Functions in Bacterial Clearance of Airways," Am. J. Respir. Cell Mol. Biol. vol. 22., 2000, pp. 665-671.*
Moskwa et al., "A Novel Host Defense System of Airways Is Defective in Cystic Fibrosis," Am J Respir Crit Care Med, vol. 175, 2007, pp. 174-183.*
Cystic Fibrosis Foundation, "Building Strength: Therapies for CF," <http://www.cff.org/treatments/Therapies/>, published Jan. 17, 2007, p. 1-2.*
Majka, G. et al., "A high-throughput method for the quantification of iron saturation in lactoferrin preparations," Anal Bioanal Chem (2013) 405:5191-5200.*
Sandre-Ballester, et al., "A Gift of Nature for the Treatment of *Pseudomonas aeruginosa* Burkholderis Cepacle and MRSA in Cystic Fibrosis Cases," Journal of Cystic Fibrosis, vol. 8, Jun. 1, 2009, p. S29 (entry #112).
Travis, et al., "Activity of Abundant Antimicrobials of the Human Airway," American Journal of Respiratory Cell and Molecular Biology, vol. 20, No. 5, May 1999, pp. 872-879.
Moskwa, et al., "A Novel Host Defense System of Airways Is Defective in Cystic Fibrosis," American Journal Respir. Crit. Care Med., vol. 175, Nov. 2, 2006, pp. 174-183, and letter to the Editor.
Childers, et al., "A New Model of Cystic Fibrosis Pathology: Lack of Transport of Glutathione and its Thiocyanate Conjugates," Medical Hypotheses, vol. 68, 2007, pp. 101-112.
Gattas, et al., "Oxidative epithelial host defense is regulated by infectious and inflammatory stimuli," Free Radical Biology & Medicine, vol. 47, 2009, pp. 1450-1458.
Conner, et al., "The Lactoperoxidase System Links Anion Transport to Host Defense in Cystic Fibrosis," FEBS Lett., Jan. 23, 2007, vol. 581 (2), pp. 271-278.
International Search Report for International PCT Application No. PCT/FR2010/000070, mailed Jun. 15, 2010.
Written Opinion for International PCT Application No. PCT/FR2010/000070, mailed Jun. 15, 2010, dated Aug. 2, 2011.

* cited by examiner

*Primary Examiner* — Tracy Vivlemore
*Assistant Examiner* — Monica Shin
(74) *Attorney, Agent, or Firm* — Oliff PLC

(57) ABSTRACT

The invention relates to the use of a synergistic combination of at least one ion selected from the group including hypothiocyanites and/or hypohalites and of lactoferrin for preparing a pharmaceutical composition for treating cystic fibrosis. In one embodiment, the lactoferrin is one having a purity higher than 95% and substantially free of lipopolysaccharides, endotoxins, and angiogenins, and having an iron saturation level higher than 15%.

7 Claims, No Drawings

USE OF A SYNERGISTIC COMBINATION OF HYPOTHIOCYANITE AND/OR HYPOHALITE IONS AND LACTOFERRIN FOR PREPARING A TREATMENT FOR CYSTIC FIBROSIS

Cystic fibrosis is a serious genetic disease; the mutation affects the protein CFTR and results in an abnormality of transfer, particularly of chloride ions.

The viscosity of the mucus is increased; it obstructs the bronchi and blocks the digestive enzyme secretions. The clinical manifestation of the disease comprises a respiratory syndrome and a digestive syndrome.

One of the main causes of death is due to the progressive colonization of the lungs by micro-organisms such as *Pseudomonas aeruginosa* and/or *Burkholderia cepacia*, or again *Staphylococcus aureus* which attack the lungs and destroy the respiratory capacities of the patients.

Recent scientific papers by the Banfi doctors, in Am. J. Respir. Grit. Care Med., 2007, 175(9): 967, Conner and Childers, have demonstrated the absence of production of the hypothiocyanite ion OSCN⁻ in persons suffering from cystic fibrosis. This ion is present naturally in the saliva and pulmonary secretions and is involved in the immune system. Its absence could explain the extreme sensitivity of the lungs of persons with the disease.

The hypothiocyanite and/or hypohalite ion is in particular generated in vivo by the lactoperoxidase system, according to the equation below:

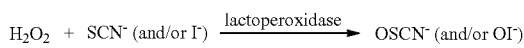

The pharmacological properties of the hypothiocyanite ion, particularly its biocidal properties, are well known, but owing to the instability of this chemical species, the half-life whereof is about 24 hours, it has not been possible to develop any formulation enabling local pulmonary treatment under satisfactory conditions.

For example, from WO2007134180 a therapeutic composition acting through the action of the hypothiocyanite ion, comprising an enzyme system, for example an oxidoreductase which produces hydrogen peroxide by reduction of a specific substrate, the specific substrate, for example glucose, the SCN⁻ ion and lactoperoxidase is known. The difficulty in formulating such therapeutic compositions is understood, as are the side effects that may be produced, for example here in the respiratory system by the in vivo production of hydrogen peroxide, which has an inflammatory and genotoxic effect and cannot be administered in long-term treatments.

In US2002/172645 the thiocyanate ion is administered alone to feed the endogenous lactoperoxidase system and form hypothiocyanite ions in vivo, or as in WO2007134180 in combination with the lactoperoxidase system.

From WO2008/003688 the demonstration of a synergy between the hypothiocyanite ion and the lactoferrin is known.

The properties of lactoferrin are in any case well known, in particular its action on biofilms and its anti-inflammatory action.

However at the present time no satisfactory formulation has been developed that enables a local treatment and particularly the destruction of bacteria which develop on the mucus of patients suffering from cystic fibrosis, and in particular on *Burkholderia cepacia*, which is highly pathogenic and particularly difficult to eradicate.

The invention relates to the use of a synergistic combination of at least one ion selected from the group of the hypothiocyanites (OSCN⁻) and/or hypohalites and of lactoferrin for preparing a pharmaceutical composition for treating cystic fibrosis and associated pulmonary infections.

In one embodiment, the invention relates to the use of a synergistic combination of at least one ion selected from the group of the hypothiocyanites (OSCN⁻) and/or hypohalites and lactoferrin for preparing a pharmaceutical composition for the treatment of infections for treating cystic fibrosis and associated pulmonary infections caused by at least one bacterium selected from the group consisting of *Burkholderia cepacia*, *Pseudomonas aeruginosa* and *Staphylococcus aureus*.

In one embodiment, it relates to the associated pulmonary infections caused by *Burkholderia cepacia*.

In one embodiment, the ion is the hypothiocyanite ion (OSCN⁻).

The hypohalite ions are selected from the group consisting of the hypoiodite, hypochlorite and hypo-bromite ions.

In one embodiment, the ion is the hypoiodite ion (OI⁻).

In another embodiment, the lactoferrin is a lactoferrin of purity higher than 95%, essentially free from endotoxin, lipopolysaccharide and angiogenin and with an iron saturation level higher than 15%.

The invention also relates to a method for therapeutic treatment of cystic fibrosis characterized in that for local treatment of the pulmonary epithelium it comprises the administration of a therapeutically active quantity of a synergistic combination of at least one ion selected from the group of the hypothiocyanites and/or hypohalites and of lactoferrin.

In fact, in cystic fibrosis the bacteria develop on the epithelium of the lungs and the treatment must be local, hence the administration will be carried out orally and/or nasally and/or by any other artificial route enabling access to the lung, for example tracheotomy.

In one embodiment, the ion is the hypothiocyanite ion (OSCN⁻).

In one embodiment, the ion is the hypoiodite ion (OI⁻).

In another embodiment, the lactoferrin is a lactoferrin having a purity higher than 95% and essentially free from lipopolysaccharides, endotoxins and angiogenins and with an iron saturation level higher than 15%.

The compositions according to the invention act by the following mechanisms:
  the lactoferrin destroys the biofilm
  the lactoferrin/OSCN⁻ combination destroys the bacteria and/or prevents their growth, and thus has a bacteriostatic and bactericidal effect.

The combination of the lactoferrin with the hypothiocyanite ion on the one hand makes it possible to reduce the concentration of hypothiocyanite in order to achieve the same anti-microbial effectiveness, and on the other hand to add the anti-inflammatory aspect to the antimicrobial aspect. Finally, the lactoferrin acts as a thinner for the expectorates which are one of the major problems in this disease.

The invention also relates to a pharmaceutical formulation intended for the treatment of the acute phases of cystic fibrosis, characterized in that it comprises 500 µM of the OSCN⁻ ion and 20 mg of Lactoferrin.

The invention also relates to a pharmaceutical formulation intended for the treatment of the acute phases of cystic fibrosis, characterized in that it comprises 250 µM of the OSCN⁻ ion and 10 mg of Lactoferrin.

The invention also relates to a pharmaceutical formulation intended for long-term treatment of cystic fibrosis, characterized in that it comprises 25 µM of the OSCN⁻ ion and 1 mg of Lactoferrin.

The invention also relates to a method of administration of a formulation according to the invention according to a dosage schedule characterized in that it comprises the twice daily administration of 5 ml of a formulation comprising 500 μM of the OSCN⁻ ion and 20 mg of Lactoferrin in the acute phases of cystic fibrosis.

The invention also relates to a method of administration of a formulation according to the invention according to a dosage schedule characterized in that it comprises the twice daily administration of 5 ml of a formulation comprising 250 μM of the OSCN⁻ ion and 10 mg of Lactoferrin in the acute phases of cystic fibrosis.

The invention also relates to a method of administration of a formulation according to the invention according to a dosage schedule characterized in that it comprises the twice daily administration of 5 ml of a formulation comprising 25 μM of the OSCN⁻ ion and 1 mg of Lactoferrin as long-term background therapy.

EXAMPLES

An extemporaneous composition for daily treatment is made by means of a self-contained portable device; it comprises 250 μM of OSCN⁻ ion, 2.4 mM of SCN⁻ ion and 2.6 mM of lactoferrin.

The preparation contains neither glucose oxidase nor lactoperoxidase, nor hydrogen peroxide (the content is measured at less than 1 ppm).

This preparation can be administered by the inhalation route by means of a sprayer and/or nebulizer and/or aerosolizer at a rate of 1 ml to 5 ml of solution per inhalation (example: inhalation of 2 ml of solution in 20 minutes) so as reach the targets within the lungs.

Pharmacological Results

The solution from the example was tested in vitro on a mucoid strain of *Pseudomonas aeruginosa*, *Burkholderia cepacia* and Methicillin Resistant *Staphylococcus Aureus*.

*Burkholderia cenocepacia* J2315 (ATCC BAA 245 known to be resistant to Tobramycin and Colistin (Holden 2009, Soiza 2004)), derived from patients with cystic fibrosis.

*Pseudomonas aeruginosa*

|  | Contact time in hours | | | | | | |
| --- | --- | --- | --- | --- | --- | --- | --- |
|  | 0 | 0.5 | 1 | 2 | 4 | 6 | 24 |
| Control | 4.14 | 4.15 | 4.16 | 4.17 | 4.16 | 4.16 | 4.13 |
| 500 μM OSCN | 4.14 | 3.23 | 3.16 | 2.98 | 2.08 | 1.90 | 1.78 |
| 250 μM OSCN + Lactoferrin | 4.14 | 2.93 | 2.89 | 2.82 | 2.15 | 1.79 | 1.51 |

(Results expressed in log CFU/ml)

*Burkholderia cepacia*

|  | Contact time in hours | | | | | | |
| --- | --- | --- | --- | --- | --- | --- | --- |
|  | 0 | 0.5 | 1 | 2 | 4 | 6 | 24 |
| Control | 4.41 | 4.47 | 4.48 | 4.54 | 4.56 | 4.58 | 4.53 |
| 500 μM OSCN | 4.41 | 3.64 | 3.56 | 3.03 | 2.08 | 1.98 | 1.78 |
| 250 μM OSCN + Lactoferrin | 4.41 | 3.42 | 3.50 | 2.99 | 2.00 | 1.84 | 1.56 |

(Results expressed in log CFU/ml)

Methicillin Resistant *Staphylococcus aureus* (MRSA)

|  | Contact time in hours | | | | | | |
| --- | --- | --- | --- | --- | --- | --- | --- |
|  | 0 | 0.5 | 1 | 2 | 4 | 6 | 24 |
| Control | 4.15 | 4.17 | 4.18 | 4.17 | 4.22 | 4.20 | 4.24 |
| 500 μM OSCN | 4.15 | 3.80 | 3.70 | 3.33 | 2.89 | 2.25 | 1.97 |
| 250 μM OSCN + Lactoferrin | 4.15 | 3.63 | 3.60 | 3.21 | 2.72 | 2.08 | 1.66 |

(Results expressed in log CFU/ml)

The solution in the example was tested in vivo on a mouse infected with a mucoid strain of *Pseudomonas aeruginosa*.

|  | Control | Treated |
| --- | --- | --- |
| Lung of mouse 72 hrs after infection | 3.1 | 1.5 |

Results expressed in log CFU/ml

The results make it possible to demonstrate a true biocidal and bactericidal action against the mucoid strains tested and the reduction in dosage of hypothiocyanite ions to be used.

The invention claimed is:

1. A pharmaceutical formulation intended for the treatment of the acute phases of cystic fibrosis, comprising 500 μM of the OSCN⁻ ion and 20 mg of lactoferrin,
   wherein the lactoferrin is a lactoferrin having a purity higher than 95% and essentially free from lipopolysaccharides, endotoxins, and angiogenin and having an iron saturation level higher than 15%, and
   wherein the pharmaceutical formulation is in an inhalable form.

2. A pharmaceutical formulation intended for the treatment of the acute phases of cystic fibrosis, comprising 250 μM of the OSCN⁻ ion and 10 mg of lactoferrin,
   wherein the lactoferrin is a lactoferrin having a purity higher than 95% and essentially free from lipopolysaccharides, endotoxins, and angiogenin and having an iron saturation level higher than 15%, and
   wherein the pharmaceutical formulation is in an inhalable form.

3. A pharmaceutical formulation intended for the long-term treatment of cystic fibrosis, comprising 250 μM of the OSCN⁻ ion and 1 mg of lactoferrin,
   wherein the lactoferrin is a lactoferrin having a purity higher than 95% and essentially free from lipopolysaccharides, endotoxins, and angiogenin and having an iron saturation level higher than 15%, and
   wherein the pharmaceutical formulation is in an inhalable form.

4. A method for the treatment of cystic fibrosis according to a dosage schedule comprising the twice daily administration to the respiratory system by inhalation of 5 ml of a formulation comprising 250 μM of the OSCN⁻ ion and 10 mg of lactoferrin for a period of four weeks in the acute phases of cystic fibrosis.

5. A method for the treatment of cystic fibrosis according to a dosage schedule comprising the twice daily administration to the respiratory system by inhalation of 5 ml of a formulation comprising 500 μM of the OSCN⁻ ion and 20 mg of lactoferrin for a period of four weeks in the acute phases of cystic fibrosis.

6. A method for the treatment of cystic fibrosis according to a dosage schedule comprising the twice daily administration to the respiratory system by inhalation of 5 ml of a formulation comprising 25 μM of the OSCN⁻ ion and 1 mg of lactoferrin as long-term background therapy.

7. A method for therapeutic treatment of cystic fibrosis, wherein for local treatment of the pulmonary epithelium, the method comprises the administration to the respiratory system by inhalation of a therapeutically active quantity of the pharmaceutical formulation of claim 1.

* * * * *